(12) United States Patent
Hibbs et al.

(10) Patent No.: US 11,191,427 B2
(45) Date of Patent: Dec. 7, 2021

(54) ENDOSCOPE UNBLOCKING FLUSH SYSTEM

(71) Applicants: Sharon A. Hibbs, Overland Park, KS (US); James E. Hibbs, Overland Park, KS (US)

(72) Inventors: Sharon A. Hibbs, Overland Park, KS (US); James E. Hibbs, Overland Park, KS (US)

(*) Notice: Subject to any disclaimer, the term of this patent is extended or adjusted under 35 U.S.C. 154(b) by 0 days.

(21) Appl. No.: 16/814,562

(22) Filed: Mar. 10, 2020

(65) Prior Publication Data

US 2020/0205649 A1 Jul. 2, 2020

Related U.S. Application Data

(63) Continuation of application No. 15/383,512, filed on Dec. 19, 2016, now Pat. No. 10,610,092.

(51) Int. Cl.
*A61B 1/12* (2006.01)
*A61B 1/015* (2006.01)
*G02B 23/24* (2006.01)

(52) U.S. Cl.
CPC ............. *A61B 1/126* (2013.01); *A61B 1/015* (2013.01); *G02B 23/2476* (2013.01)

(58) Field of Classification Search
None
See application file for complete search history.

(56) References Cited

U.S. PATENT DOCUMENTS

| 6,481,462 | B2 | 11/2002 | Fillmore et al. |
| 8,251,945 | B2* | 8/2012 | Secrest ............ A61B 1/00068 604/35 |
| 2011/0065997 | A1 | 5/2011 | Hamer et al. |
| 2011/0105838 | A1 | 5/2011 | Fogel |
| 2012/0088975 | A1* | 4/2012 | Morimoto ............ A61B 1/015 600/159 |
| 2012/0116168 | A1* | 5/2012 | Mollstam ............ A61M 1/0058 600/155 |

* cited by examiner

*Primary Examiner* — Cristi J Tate-Sims
(74) *Attorney, Agent, or Firm* — Erickson Kernell IP, LLC; John C McMahon

(57) ABSTRACT

An endoscope unblocking flush system for back flushing a suction lumen of an endoscope includes a flush source providing pressurized water and a valve mechanism to cut off a suction source from the suction lumen and to open the suction lumen to flow of back flush water from the flush source. The valve mechanism includes a valve housing with ports to connect to the suction lumen, the suction source, and the flush source. A valve member within the housing has passages to connect the suction source to the suction lumen in a run state and to connect the flush source to the suction lumen in a flush state.

11 Claims, 4 Drawing Sheets

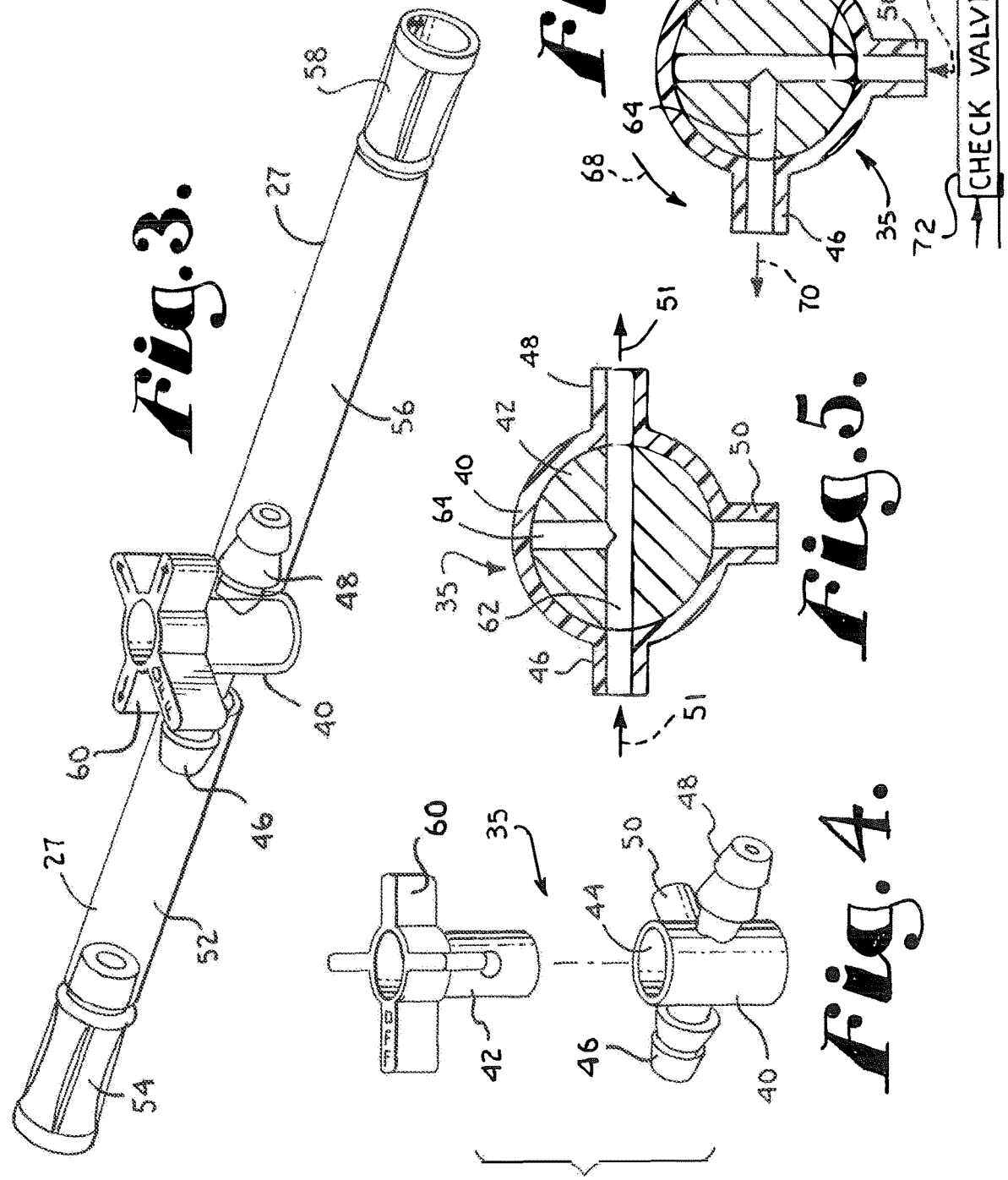

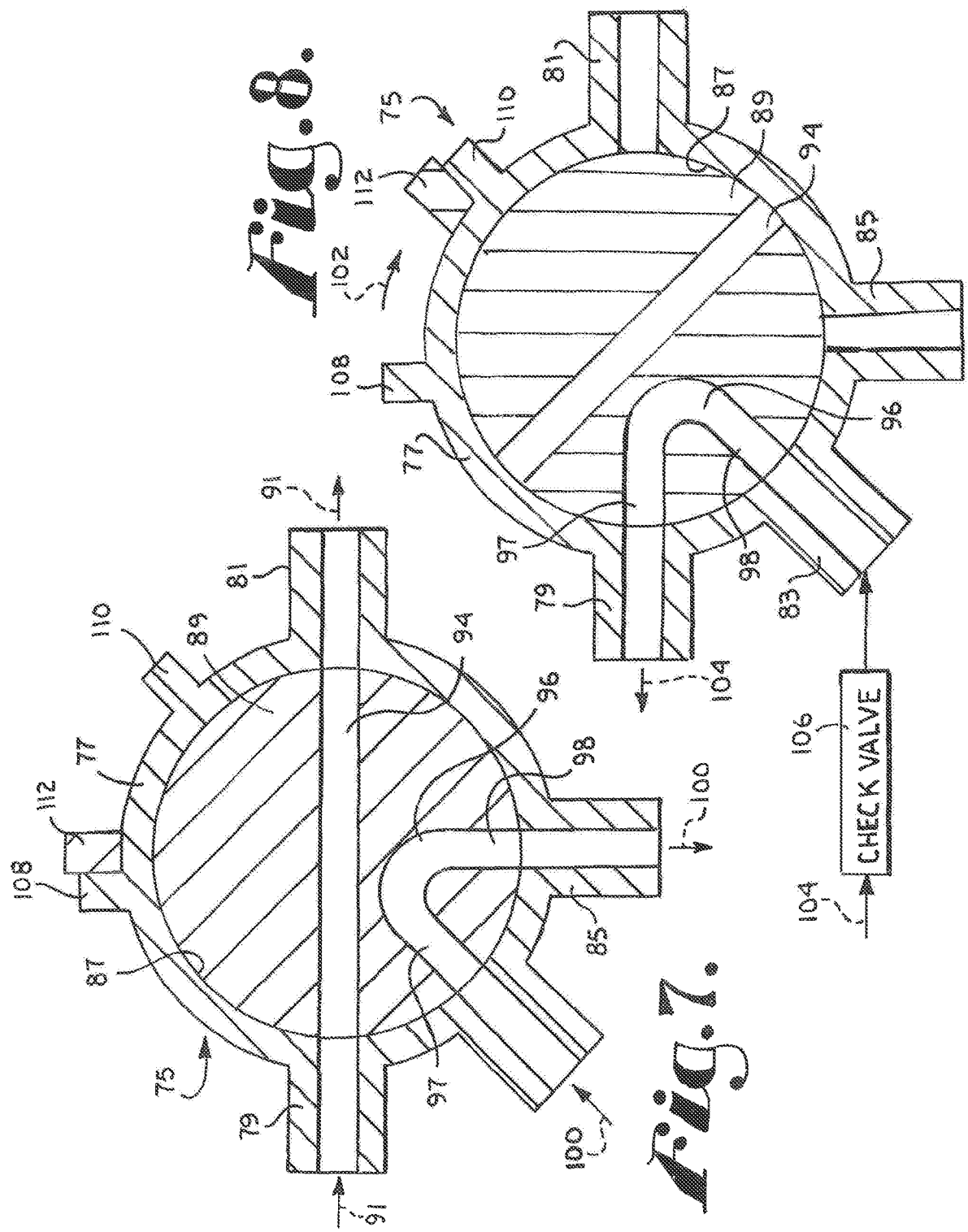

ENDOSCOPE UNBLOCKING FLUSH SYSTEM

CROSS-REFERENCE TO RELATED APPLICATIONS

This application is a continuation of U.S. patent application Ser. No. 15/383,512, filed Dec. 19, 2016, the contents of which are incorporated herein by reference.

BACKGROUND OF THE INVENTION

The present invention is broadly concerned with improvements in endoscopes and endoscope systems and, more particularly, to an improved flush apparatus or system for unclogging a lumen or line of an endoscope.

Endoscopes and endoscopic devices provide capabilities for physicians to view internal regions of the body for diagnostic and treatment purposes. A typical endoscope may include a rigid or flexible tube; a light delivery system to illuminate the organ or object under inspection including light source which is normally outside the body, the light being carried by an optical fiber system extending through an endoscope tube; and a lens system to capture an image within the organ being viewed which is usually transferred to an eyepiece or an image array by fiberoptics. Alternatively, endoscopes may incorporate a miniature image array at the distal end of the endoscope tube, with data representing the image conveyed to electronics by electrical conductors. An image captured by the image array may be displayed in a display monitor.

Many endoscopes include lumens or passages connected to sources for delivering air or water to nozzles at the end of the endoscope tube and for suction. The endoscope system may include valves to control the flow of air or water or the suction of materials from the site of interest. The endoscope may also include one or more passages for the insertion of surgical instruments through the endoscope to the distal end thereof. Some endoscopes incorporate steering mechanisms therein to control the direction of travel of the distal ends thereof.

In the use of endoscopes, the suction lumen communicates with a vacuum pump by way of a suction line. The suction function is used to remove materials from the organ under examination, such as fluids used to lubricate passage through the organ or to clean off the lens. Such fluids may sometimes include solid materials entrained therein which can cause a blockage in the suction lumen, often in the vicinity of the suction valve. If the blockage cannot be cleared by suction alone, it is often necessary to back flush the suction lumen. Typically, the procedure is to disconnect the suction line from a suction fitting and to connect a syringe filled with water which is injected into the suction line to clear the blockage in the suction lumen. Afterwards, the suction line must be disconnected from the syringe and reconnected to the suction fitting of the vacuum pump. Such a procedure is time-consuming and may have to be performed repeatedly, since multiple blockages can occur.

SUMMARY OF THE INVENTION

The present invention provides embodiments of an improved apparatus for selectively flushing a lumen of an endoscope to remove a blockage therein. An embodiment of an endoscope unblocking flush system or apparatus according to the present invention comprises: a flush source having a flush fluid which can be pressurized; a flush valve mechanism communicating with the lumen of the endoscope and the flush source; and the flush valve mechanism having a run state in which operational communication through the lumen is enabled a flush state in which operational communication through such a lumen of an endoscope is prevented and in which the flush source communicates with the lumen whereby pressurization of the flush source urges the flush fluid through the lumen endoscope to clear a blockage therein. The lumen to be flushed may be a suction lumen of the endoscope. The flush source fluid may be water and may be received from an irrigation water source which is otherwise used to provide water to a water lumen of the endoscope.

The flush valve mechanism may include an endoscope port, a source port, and a flush port with the flush valve mechanism enabling operational communication between the source port and the endoscope port in the run state of the flush valve mechanism. The flush port communicates with the flush source whereby the flush valve mechanism prevents communication between the source port and the endoscope port and enables communication between the flush port and the endoscope port in the flush state of the flush valve mechanism such that the flush fluid can be urged into the flush port and out the endoscope port.

The flush valve mechanism may include a valve housing including a suction port, an endoscope port, and a flush port and a valve member positioned within the valve housing and movable between a run position in the run state of the flush valve mechanism and a flush position in the flush state of the flush valve mechanism. The valve member may have a run passage positioned to enable operational communication through a lumen of an endoscope in the run state of the flush valve mechanism and a flush passage positioned to enable communication between the flush source and a lumen of an endoscope in the flush state of the flush valve mechanism. The valve housing may include a run stop engaged by the valve member in the run position and a flush stop engaged by the valve member in the flush position. The valve member may be rotatably movable between the run position and the flush position.

In an embodiment of the endoscope flush apparatus, the valve housing has a substantially cylindrical valve chamber therein with the source port diametrically aligned with the endoscope port and the flush port being substantially perpendicular to a run axis extending from the source port to the endoscope port. The valve member is substantially cylindrical and is sealingly rotatable within the cylindrical valve chamber. The valve member includes a substantially diametric run passage positioned to align with the run axis extending from the source port to the endoscope port in the run position of the valve member. The valve member also includes a substantially radial flush passage extending substantially perpendicular to the run passage with the flush passage communicating between the endoscope port and the run passage communicating with the flush port in the flush position of the valve member to enable communication between the flush port and the endoscope port in the flush position of the valve member.

In an embodiment of the endoscope flush apparatus, the valve housing has a substantially cylindrical valve chamber therein with the source port diametrically aligned with the endoscope port. The housing also has an irrigation port substantially perpendicular to a run axis extending from the source port to the endoscope port and the flush port positioned angularly between the irrigation port and the endoscope port. The valve member includes a substantially diametric run passage positioned to align with the run axis extending from the source to the endoscope port in the run position of the valve member. The valve member also includes a flush passage with a first branch which aligns with the irrigation port in the run position and with the flush port in the flush position of the valve member and a second branch communicating with the first branch and positioned angularly thereto which aligns with the flush port in the run position and with the endoscope port in the flush position to thereby enable communication between the flush port and the irrigation port in the run position and communication between the flush port and the endoscope port in the flush position.

The valve housing may include a run stop engaged by the valve member in the run position and a flush stop engaged by the valve member in the flush position. The flush source may include a water source which normally provides irrigation water for injection into the organ under examination to clean the lens, for lubrication purposes or the like. Typically, the irrigation water source is pressurized and provides water to a water lumen of the endoscope by way of a water valve. In an embodiment of the endoscope flush apparatus, flush valve mechanism enables communication of irrigation water from the irrigation water source to an irrigation lumen of an endoscope in the run state of the flush valve mechanism and enables communication of flush water to the suction lumen of an endoscope in the flush state to clear a blockage therein.

Various objects and advantages of the present invention will become apparent from the following description taken in conjunction with the accompanying drawings wherein are set forth, by way of illustration and example, certain embodiments of this invention.

The drawings constitute a part of this specification, include exemplary embodiments of the present invention, and illustrate various objects and features thereof.

BRIEF DESCRIPTION OF THE DRAWINGS

FIG. 3 is an enlarged perspective view of a suction conduit having an embodiment of a flush valve of the present invention positioned therein.

FIG. 4 is an exploded perspective view of an embodiment of the flush valve of the present invention, showing a valve body and handle removed from a valve housing of the valve.

FIG. 5 is an enlarged diagrammatic cross sectional view of a first embodiment of the flush valve of the present invention with a valve body shown in a run position relative to the valve housing.

FIG. 6 is a view similar to FIG. 5 and shows the valve body of the first embodiment of the flush valve in a flush position relative to the valve housing.

FIG. 7 is an enlarged diagrammatic cross sectional view of a second embodiment of the flush valve with a valve body shown in a run position relative to a valve housing.

FIG. 8 is a view similar to FIG. 7 and shows the valve body in a flush position relative to the valve housing.

DETAILED DESCRIPTION OF THE INVENTION

Figure 1:
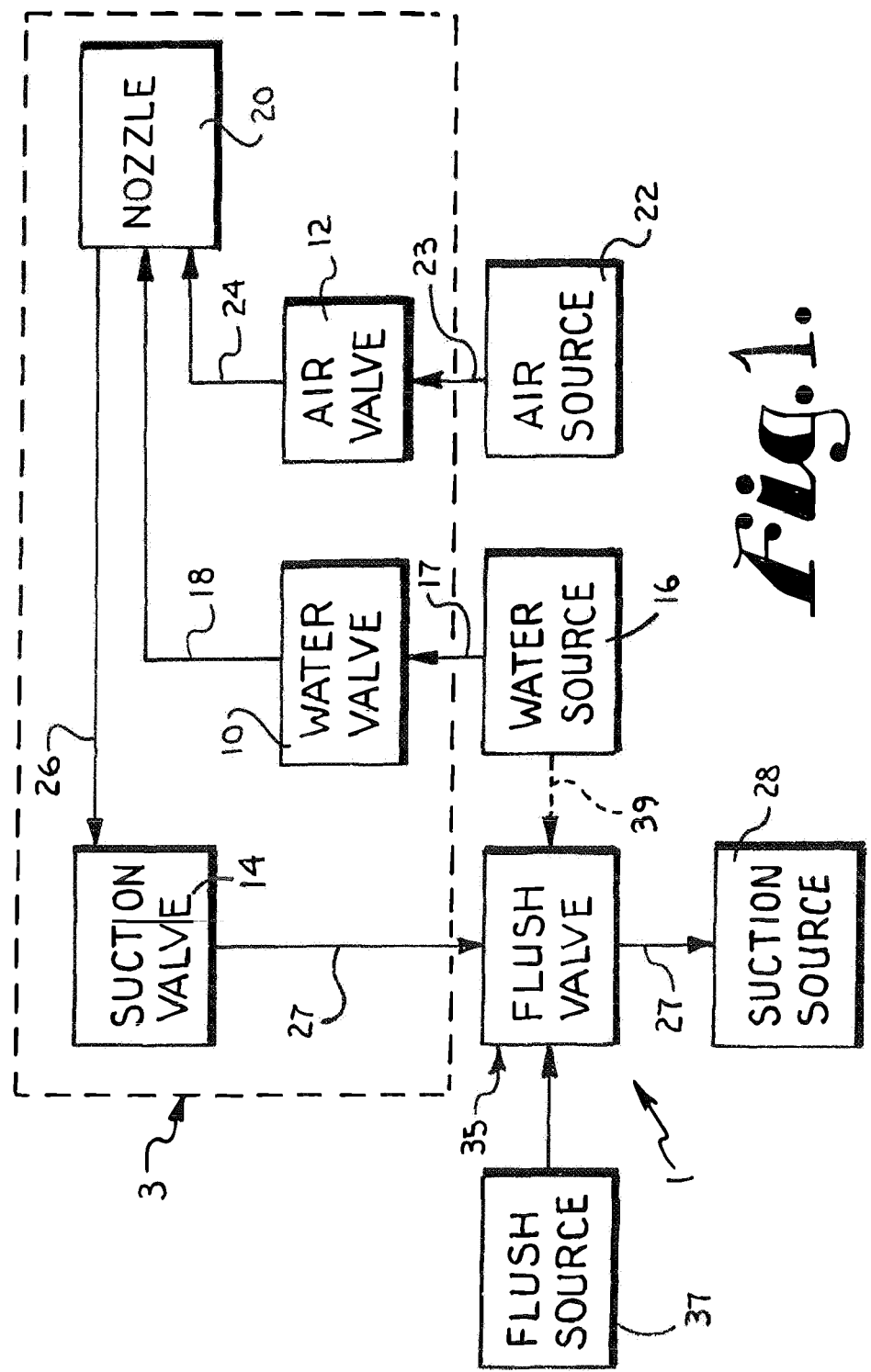
FIG. 1 is a simplified block diagram showing components of an endoscope system incorporating a flush valve apparatus according to the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates an embodiment of an endoscope unblocking flush system or apparatus according to the present invention for use in cooperation with an endoscope system 2. The system 2 includes an endoscope instrument or endoscope 3 along with supporting equipment, as will be described below.

Figure 2:
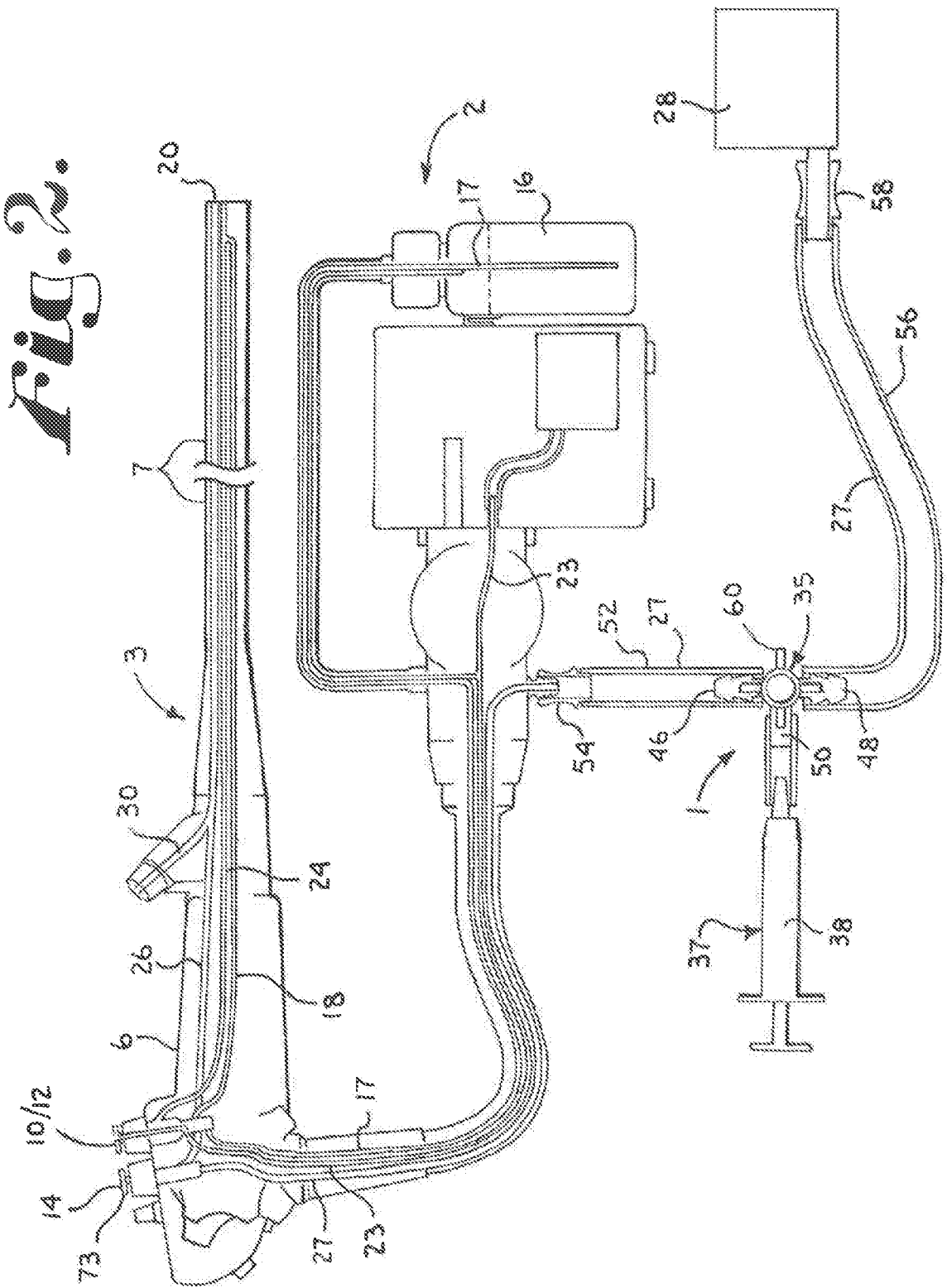
FIG. 2 is a diagrammatic view showing components of the endoscope system and showing an embodiment of a flush valve apparatus according to the present invention.

Referring to FIGS. 1 and 2, the endoscope instrument 3 is conventional in configuration and includes a control section 6 at a proximal end and an elongated tube assembly 7 extending from the control section 6. The length and degree of flexibility of the tube assembly 7 depends on the intended use of the endoscope 3.

The control section 6 includes a water valve 10, an air valve 12, and a suction valve 14. As shown in FIG. 2, the water and air valves 10 and 12 may be combined into a single control. The water valve 10 controls the flow of pressurized water from an irrigation water source 16 through a water line 17 to the water valve 10 to a water lumen 18 extending from the control section 6 through the endoscope tube assembly 7 to a nozzle end 20 of the tube assembly 7. The term "lumen" as used herein is intended to encompass a channel, passage, conduit, pipe, tube, or the like which is capable of carrying a fluid therethrough. Similarly, the air valve 12 controls the flow of pressurized air from an air source or air pump 22 through an air line 23 to the air valve 12 to an air lumen 24 extending through the tube assembly 7 to the nozzle end 20 thereof. In an opposite directional sense, the suction valve 14 controls the flow of air, possibly with other materials entrained therein, from the nozzle end 20 of the tube assembly 7 through a suction lumen 26 extending to the suction valve 14 through the tube assembly 7 to a suction line 27 extending to a suction or vacuum source 28, such as a suction or vacuum pump.

In the illustrated endoscope instrument 3, the suction lumen 26 has a tool branch 30 (FIG. 2) which allows a surgical tool (not shown) to be extended toward the nozzle end 20 through the suction lumen 26. The tool branch 30 is preferably capable of being sealed or is self-sealing when a surgical tool is not present. It is foreseen that the endoscope 3 may, alternatively, have a tool lumen (not shown) independent of the suction lumen.

Although not illustrated in FIG. 2 to simplify the figure, the endoscope 3 incorporates conventional endoscope optics to convey an image from the nozzle end 20 to a remote location. Such optics may include a lens (not shown) at the nozzle end 20 along with either fiberoptics (not shown) to transfer an image remotely or an electronic array (not shown) cooperating with the lens to record an image along with interface circuitry (not shown) and electrical conductors (not shown) to convey data representing the image recorded by the array to a remote location for viewing.

Referring particularly to FIG. 2, the suction lumen 26 can become clogged upon drawing solid materials out of a patient's organ during examination or a procedure. If repeated attempts to clear the blockage by operation of the suction valve 14 are not successful, the suction lumen 26 is typically back flushed with water. This requires disconnection of the suction line 27 from the suction pump 28, after disabling it, and the connection of a syringe to the suction line 27. Afterwards, the syringe is disconnected, and the suction line 27 is reconnected to the suction pump 28, which is then re-enabled. As stated previously, the procedure be required multiple times to successfully clear the blockage.

In the present invention, the endoscope unblocking flush apparatus 1 is connected in the suction line 27 to facilitate back flushing of an endoscope lumen, such as the suction lumen 26. The apparatus 1 generally includes a flush valve mechanism 35 connected in the suction line 27 and a flush source 37 which is operated to supply a fluid under pressure, such as water, to back flush the suction lumen 26 by way of a portion of the suction line 27. The valve mechanism 35 has a run state or position in which flow through the suction line 27 is unimpeded and a flush state or position in which flow to the suction pump 28 is prevented and in which the flush source 37 communicates with the suction lumen 26 through a section of the suction line 27.

As illustrated in FIG. 2, the flush source 37 may be a syringe 38 filled with water which is manually injected into the suction lumen 26 through a section of the suction line 27. Alternatively, other configurations of flush sources are foreseen, such as the irrigation water source 16, as indicated by the line 39 between the flush valve 35 and the water source 16 in FIG. 1, with appropriate valving as will be described below. The flush apparatus 1 can stay connected in the suction line 27 throughout the procedure using the endoscope 3. For this reason, multiple cycles of back flush with the valve mechanism 35 in the flush position, followed by operation of the suction valve 14 with the valve mechanism in the run position, can more expeditiously clear a blockage in the suction lumen 26.

Referring to FIGS. 3 through 6, an embodiment of the valve mechanism 35 includes a valve housing 40 having a valve member 42 rotatably received therein. The illustrated valve housing 42 has a cylindrical valve housing chamber 44 in which a compatibly cylindrical valve member 42 is received. The chamber 44 is preferably closed at one end. The valve housing 40 has fittings forming an endoscope port 46, a suction port 48, and a flush port 50. In the illustrated valve housing 40, the endoscope port 46 and the suction port 38 are aligned diametrically along a run axis indicated by the aligned arrows 51 in FIG. 5, with the flush port 50 perpendicular to the run axis. The apparatus 1 may include an endoscope side conduit 52 (FIG. 3) with an endoscope side fitting 54 and a suction side conduit 56 with a suction side fitting 58 for connecting the valve housing 40 in the suction line 27. As such, the conduits 52 and 56 form components of the suction line 27. The illustrated valve member 42 has a valve handle 60 extending therefrom to rotate the valve member 42 between a run position, in the run state of the valve mechanism 35, and a flush position in the flush state of the valve mechanism 35.

Referring to FIGS. 5 and 6, the illustrated valve member 42 includes a run passage 62 and a flush passage 64. In the embodiment illustrated, the run passage 62 is oriented diametrically to the valve member 42 and provides communication between the endoscope port 46 and the suction port 48 in the run position shown in FIG. 5. The flush passage 64 is substantially perpendicular or radial to the run passage 62 and communicates therewith. In the run position, the flush passage 64 is sealed against the valve housing 40. Thus, when the suction valve 14 is operated, flow from the suction lumen 26 toward the suction pump 28 is unimpeded, as indicated by direction of the arrows 51 in FIG. 5.

When the valve member 42 is rotated a quarter turn to the flush position shown in FIG. 6, indicated by the arrow 68, the flush passage 64 is aligned with the endoscope port 46 and one end of the run passage 62 is aligned with the flush port 50, with the opposite end of the run passage 62 sealed against the valve housing 40. Thus, communication from the flush port 50 to the endoscope port 46 is provided, as indicated by arrows 70, thereby providing communication from the flush source 37 toward the suction lumen 26. In an embodiment of the apparatus 1, there is a check valve 72 (FIG. 6) positioned between the flush source 37 and the flush port 50 to prevent possible back flow through the valve apparatus 35 into the flush source 37 and possible contamination thereof. While the illustrated valve mechanism 35 is provided with the valve handle 60 for manual operation, it is foreseen that the valve mechanism 35 could be motorized and operated remotely, as by a foot switch (not shown) or the like. During a back flush procedure, the suction valve operator stem 73 (FIG. 2) may be removed from the suction valve structure 14 to provide maximum clearance in the suction line 26 to facilitate clearing any blockage therein. While the stem 73 is removed, the opening therefor is blocked externally, as by placing a finger thereover.

FIGS. 7 and 8 illustrate an irrigation embodiment 75 of the flush valve mechanism which uses the irrigation water source 16 (FIG. 1) as a flush source 37. The valve mechanism 75 includes a valve housing 77 having an endoscope port 79, a suction port 81, a flush port 83, and an irrigation port 85. The valve housing 77 has a cylindrical chamber 87 therein to rotatably receive a cylindrical valve member 89. The endoscope port 83 and suction port 81 are positioned in diametric relation along a run axis indicated by the aligned arrows 91 in FIG. 7. The irrigation port 85 is positioned perpendicular to the run axis, while the flush port 83 is positioned at a 45° angle between the endoscope port 79 and the irrigation port 85.

The endoscope port 79 is connected to the suction line 27, as by a conduit similar to the conduit 52 (FIG. 3), to communicate with the suction lumen 26 of the endoscope 3. The suction port 81 is connected to the suction line 27, as by a conduit similar to the conduit 56 (FIG. 3), to communicate with the suction source 28. The irrigation port 85 is connected by way of the water line 17 to the water lumen 18 of the endoscope 3. The flush port 83 is connected to the water source 16, which functions as the flush source 37.

The valve member 89 has a run passage 94 extending diametrically thereacross. The valve member 89 has a flush passage 96 which is independent of the run passage 94 and which has a first branch 97 and a second branch 98. In a run position of the valve mechanism 75 shown in FIG. 7, the run passage 94 is aligned with the endoscope port 79 and the suction port 81 whereby suction can flow therebetween, as indicated by the direction of the arrows 91. The valve member 89 may be operatively moved in a manner similar to the valve member 42, that is, by manual rotation or by motorized rotation.

In the run position, the flush passage 96 is oriented with the first branch 97 aligned with the flush port 83 and the second branch 98 aligned with the irrigation port 85. This enables irrigation water to flow from the water source 16 through the flush port 83 and the irrigation port 85, as indicated by the arrows 100 to the water lumen 18 when the water valve 10 is operated.

In a flush position of the valve mechanism 75 shown in FIG. 8, the valve member 89 is turned 45°, as indicated by the arrow 1. In the flush position, the run passage is sealed at both ends, while the first branch 97 of the flush passage 96 is aligned with the endoscope port 79 and the second branch 98 is aligned with the flush port 83. This enables flushing water to flow from the water source 16 through the flush port 83 and the endoscope port 79 to the suction lumen 26 when the water valve 10 is operated, as indicated by the arrows 104 in FIG. 8, to thereby back flush the suction lumen. In an embodiment of the apparatus 1, there is a check valve 106 (FIG. 8) positioned between the water source 16, which functions as the flush source 37, and the flush port 83 to prevent possible back flow through the valve mechanism 75 into the water source 16 and possible contamination thereof.

The illustrated valve mechanism 75 is provided with a positive means for positively locating the valve member 89 in the run position or the flush position. The illustrated valve housing includes a run position stop 108 and a flush stop 110 extending radially therefrom. The valve member 89 has a stop lug 112 extending radially and sealingly therefrom. The stops 108 and 110 are positioned so that the stop lug 112 engages the run position stop 108 in the run position of the valve member 89, as shown in FIG. 7, and the flush position stop 110 in flush position of the valve member 89, as shown in FIG. 8. It is foreseen that the valve mechanism 35 may have stops and a stop lug (not shown) similar to the stops 108 and 110 and stop lug 112 of the valve mechanism 75.

It is to be understood that while certain forms of the present invention have been described and illustrated herein, it is not to be limited to the specific forms or arrangement of parts described and shown.

What is claimed and desired to be secured by Letters Patent is:

1. A flush apparatus for flushing a suction lumen of an endoscope to clear a blockage thereof and comprising:
   (a) a suction source communicating with a suction lumen of an endoscope by way of a suction line;
   (b) a flush source having a flush fluid which can be pressurized;
   (c) a flush valve mechanism having the suction line and the flush source connected thereto;
   (d) the flush valve mechanism having a run state in which communication through the suction line from the suction source to a suction lumen of an endoscope is enabled;
   (e) the flush valve mechanism having a flush state in which communication from the suction source through the suction line is prevented and in which the flush source communicates with the suction line whereby pressurization of the flush source urges the flush fluid through the suction line to clear a blockage in a suction lumen of an endoscope;
   (f) a valve housing including a suction port communicating with the suction source, an endoscope port communicating with suction lumen, and a flush port communicating with the flush source;
   (g) a valve member positioned within the valve housing and movable between a run position in the run state of the flush valve mechanism, with the suction port communicating with the endoscope port, and a flush position in the flush state of the flush valve mechanism with the flush port communicating with the endoscope port;
   (h) the valve housing has a substantially cylindrical valve chamber therein with the source port diametrically aligned with the endoscope port and the flush port being substantially perpendicular to a run axis extending from the source port to the endoscope port;
   (i) the valve member is substantially cylindrical and is sealingly rotatable within the cylindrical valve chamber;
   (j) the valve member includes a substantially diametric run passage positioned to align with the run axis extending from the source port to the endoscope port in the run position of the valve member; and
   (k) the valve member includes a substantially radial flush passage extending substantially perpendicular to the run passage, the flush passage communicating with the endoscope port and the run passage communicating with the flush port in the flush position of the valve member to enable communication between the flush port and the endoscope port in the flush position of the valve member.

2. An apparatus as set forth in claim 1 wherein the flush valve mechanism includes:
   (a) an endoscope port, a source port, and a flush port;
   (b) the flush valve mechanism enabling operational communication between the source port and the endoscope port in the run state of the flush valve mechanism;
   (c) the flush port communicating with the flush source; and
   (d) the flush valve mechanism preventing communication between the source port and the endoscope port and enabling communication between the flush port and the endoscope port in the flush state of the flush valve mechanism whereby the flush fluid can be urged into the flush port and out the endoscope port.

3. An apparatus as set forth in claim 1 wherein the flush valve mechanism includes:
   (a) a run passage positioned to enable operational communication through the suction line in the run state of the flush valve mechanism; and
   (b) a flush passage positioned to enable communication between the flush source and the suction line in the flush state of the flush valve mechanism.

4. An apparatus as set forth in claim 1 wherein the valve member includes:
   (a) a run passage positioned to enable communication from the suction source to the suction lumen in the run state of the flush valve mechanism; and
   (b) a flush passage positioned to enable communication between the flush source and the suction lumen in the flush state of the flush valve mechanism.

5. An apparatus as set forth in claim 1 wherein the valve housing includes:
   (a) a run stop engaged by the valve member in the run position; and
   (b) a flush stop engaged by the valve member in the flush position.

6. An apparatus as set forth in claim 1 wherein:
   (a) the flush source includes a water source which provides irrigation water;
   (b) the flush valve mechanism enables communication of irrigation water from the water source to an irrigation lumen of an endoscope in the run state of the flush valve mechanism; and
   (c) the flush valve mechanism enables communication of flush water from the water source to the suction lumen of an endoscope in the flush state.

7. A flush apparatus for flushing a suction lumen of an endoscope to clear a blockage thereof and comprising:
   (a) a suction source communicating with a suction lumen of an endoscope by way of a suction line;
   (b) a flush source having a flush fluid which can be pressurized;
   (c) a flush valve mechanism having the suction line and the flush source connected thereto;

(d) the flush valve mechanism having a run state in which communication through the suction line from the suction source to a suction lumen of an endoscope is enabled;

(e) the flush valve mechanism having a flush state in which communication from the suction source through the suction line is prevented and in which the flush source communicates with the suction line whereby pressurization of the flush source urges the flush fluid through the suction line to clear a blockage in a suction lumen of an endoscope;

(f) a valve housing including a suction port communicating with the suction source, an endoscope port communicating with suction lumen, and a flush port communicating with the flush source;

(g) a valve member positioned within the valve housing and movable between a run position in the run state of the flush valve mechanism, with the suction port communicating with the endoscope port, and a flush position in the flush state of the flush valve mechanism with the flush port communicating with the endoscope port;

(h) the valve housing has a substantially cylindrical valve chamber therein with the source port diametrically aligned with the endoscope port and an irrigation port being substantially perpendicular to a run axis extending from the source port to the endoscope port;

(i) the valve housing has the flush port positioned angularly between the irrigation port and the endoscope port;

(j) the valve member is substantially cylindrical and is sealingly rotatable within the cylindrical valve chamber;

(k) the valve member includes a substantially diametric run passage positioned to align with the run axis extending from the source port to the endoscope port in the run position of the valve member; and (l) the valve member includes a flush passage with a first branch which aligns with the irrigation port in the run position and with the flush port in the flush position of the valve member and a second branch communicating with the first branch and positioned angularly thereto which aligns with the flush port in the run position and with the endoscope port in the flush position to thereby enable communication between the flush port and the irrigation port in the run position and communication between the flush port and the endoscope port in the flush position.

8. A flush apparatus for flushing a suction lumen of an endoscope to clear a blockage thereof and comprising:

(a) a suction source communicating with a suction lumen of an endoscope by way of a suction line;

(b) a flush source having a flush fluid which can be pressurized;

(c) a flush valve mechanism including a valve housing and a valve member positioned within the valve housing and movable between a run position and a flush position;

(d) the valve housing including a suction port communicating with the suction source, an endoscope port communicating with suction lumen, and a flush port communicating with the flush source;

(e) the valve member including a run passage which enables communication between the suction port and the endoscope port in the run position;

(f) the valve member including a flush passage which enables communication between the flush source and the endoscope port in the flush position and being configured to prevent communication between the suction port and the endoscope port in the flush position;

(g) the valve housing has a substantially cylindrical valve chamber therein with the source port diametrically aligned with the endoscope port and the flush port being substantially perpendicular to a run axis extending from the source port to the endoscope port;

(h) the valve member is substantially cylindrical and is sealingly rotatable within the cylindrical valve chamber;

(i) the run passage is a substantially diametric run passage positioned to align with the run axis extending from the source port to the endoscope port in the run position of the valve member; and (j) the flush passage is a substantially radial flush passage extending substantially perpendicular to the run passage, the flush passage communicating with the endoscope port and the run passage communicating with the flush port in the flush position of the valve member to enable communication between the flush port and the endoscope port in the flush position of the valve member.

9. A flush apparatus for flushing a suction lumen of an endoscope to clear a blockage thereof and comprising:

(a) a suction source communicating with a suction lumen of an endoscope by way of a suction line;

(b) a flush source having a flush fluid which can be pressurized;

(c) a flush valve mechanism including a valve housing and a valve member positioned within the valve housing and movable between a run position and a flush position;

(d) the valve housing including a suction port communicating with the suction source, an endoscope port communicating with suction lumen, and a flush port communicating with the flush source;

(e) the valve member including a run passage which enables communication between the suction port and the endoscope port in the run position;

(f) the valve member including a flush passage which enables communication between the flush source and the endoscope port in the flush position and being configured to prevent communication between the suction port and the endoscope port in the flush position;

(g) the valve housing has a substantially cylindrical valve chamber therein with the source port diametrically aligned with the endoscope port and an irrigation port being substantially perpendicular to a run axis extending from the source port to the endoscope port;

(h) the valve housing has the flush port positioned angularly between the irrigation port and the endoscope port;

(i) the valve member is substantially cylindrical and is sealingly rotatable within the cylindrical valve chamber;

(j) the flush passage is a substantially diametric run passage positioned to align with the run axis extending from the source port to the endoscope port in the run position of the valve member; and (k) the flush passage includes a first branch which aligns with the irrigation port in the run position and with the flush port in the flush position of the valve member and a second branch communicating with the first branch and positioned angularly thereto which aligns with the flush port in the run position and with the endoscope port in the flush position to thereby enable communication between the flush port and the irrigation port in the run position and communication between the flush port and the endoscope port in the flush position.

10. An apparatus as set forth in claim 9 wherein the valve housing includes:
(a) a run stop engaged by the valve member in the run position; and
(b) a flush stop engaged by the valve member in the flush position.

11. An apparatus as set forth in claim 9 wherein:
(a) the flush source includes a water source which provides irrigation water;
(b) the flush valve mechanism enables communication of irrigation water from the water source to an irrigation lumen of an endoscope in the run position of the valve member; and
(c) the flush valve mechanism enables communication of flush water from the water source to the suction lumen of an endoscope in the flush position of the valve member.

* * * * *